United States Patent
Nagai et al.

(10) Patent No.: US 6,238,920 B1
(45) Date of Patent: May 29, 2001

(54) CULTURE AND TRANSPORTATION OF BOVINE EMBRYOS

(75) Inventors: Takashi Nagai, Tsukuba; Akira Okano, Kashiwa; Masashi Takahashi, Tsukuba; Takayoshi Kariya, Sapporo; Hiroya Kadokawa, Sapporo; Hitomi Hirako, Sapporo; Masashige Kuwayama, Yokohama; Seizo Hamano, Tokyo, all of (JP)

(73) Assignees: Director of National Institute of Animal Industry, Ministry of Agriculture, Forestry and Fisheries, Inashiki-gun; Director of Livestock Improvement Association, Tokyo, both of (JP)

( * ) Notice: Subject to any disclaimer, the term of this patent is extended or adjusted under 35 U.S.C. 154(b) by 0 days.

(21) Appl. No.: 08/018,546

(22) Filed: Feb. 17, 1993

(51) Int. Cl.$^7$ .................................................. C12N 5/02
(52) U.S. Cl. ........................ 435/374; 435/325; 435/383
(58) Field of Search ....................... 435/240.1, 240.2, 435/240.25, 240.3, 1, 2, 374, 325, 383

(56) References Cited

PUBLICATIONS

Takahashi et al., Thereogenology, 39(1), p. 326, Jan. 1993.*
Ealy et al., Cell Biology International Reports, vol. 16, No. 2, pp. 125–131, Feb. 1992.*
Hasler et al, J. of Animal Science, vol. 49, Supplement I, pp 135–136, Feb. 1979.*
Bannai, Hum. Cell, 5 (3), pp. 292–297, Sep. 1992 (Biosis Abstrat).*

* cited by examiner

Primary Examiner—Jon P. Weber
(74) Attorney, Agent, or Firm—Oblon, Spivak, McClelland, Maier & Neustadt, P.C.

(57) ABSTRACT

A method of culturing bovine embryos by culturing said bovine embryos in a medium containing thiol compound, and also a method of transporting bovine embryos by transporting said bovine embryos in a medium containing thiol compound are disclosed.

According to the present invention, it is possible to culture bovine embryos up to blastocyst stage efficiently in the medium containing low molecular thiol compound without in vivo culture or coculture using feeder cells. Also when low molecular thiol compound is added to the transportation medium for bovine embryos, almost 100% embryos are still viable after long distant transportation.

5 Claims, No Drawings

CULTURE AND TRANSPORTATION OF BOVINE EMBRYOS

FIELD OF THE INVENTION

This invention relates to a method of culturing or transporting effectively bovine embryos for transplanting.

BACKGROUND OF THE INVENTION

So far bovine embryos obtained by in vitro fertilization and/or in vivo fertilization have been cultured for several days in in vivo (oviducts of rabbits and sheep) or in vitro (co-culture in the presence of oviductal or cumulus cells) for their development.

When bovine embroys obtained by in vitro culture of in vitro fertilized oocytes were transported to the distant place where the embryo transfer of them was carried out, they were cryopreserved using glycerol and sucrose as cryoprotectans, stored and transported in liquid nitrogen. However, this method of transportation of embryos is nothing but a trial.

It is well known that bovine embryos do not develop beyond 8 cell stage (8 cell block) in in vitro culture. To overcome this 8 cell block embryos have been cultured in vivo or in vitro (co-culture with a monolayer of cells).

However, it is time and effort consuming to culture embryos in vivo, because embryos must be transferred to recipient animals and collected from them surgically. In addition, as for culturing embryos with supporting (oviduotal or cumulus) cells in vitro, establishment of those cells is also time and effort consuming. Furthermore, sometimes the supporting cells cover the surface of bovine embryos resulting in distortion of the embryos. Therefore, it is necessary to develop more efficient in vitro culture system for bovine embryos.

When bovine embryos are transported to the distant place after cryopreservation, the viability of them decreases sharply during freezing and thawing of them. In addition, before transfer of cryopreserved embryos, a special facility for treatment of the cryopreserved embryos and examination of the viability of the embryos after thawing are needed. Therefore, it is necessary to develope a handy and reliable method for the transportation of bovine embryos.

While we have been investigating the suitable culture and transportation methods for bovine embryos, we found out that the reduced state of embryos during culture and transportation are important for them to develop. And we concluded that low molecular thiol compounds are suitable to make intracellular conditions of embryos reduced state and completed a new method of culture or transportation of bovine embryos.

SUMMARY OF THE INVENTION

This invention provides methods for culture and transportation of bovine embryos. In particular, the present invention relates a method for culture or transportation of bovine embryos which comprises adding thiol compound, especially low molecular thiol compound to a medium for culture or transportation of them.

DETAILED DESCRIPTION OF THE INVENTION

In this invention, low molecular thiol compounds are low molecular compounds that have thiol, such as β-mercaptoethanol (hereinunder it may be abbreviated as β-ME, molecular weight (m.w.):78.13) , β-mercaptoethylamine (hereinunder it may be abbreviated as cysteamine, m.w.:77.14), glutathione (m.w.:307.3), dithiothreitol (m.w.:154.24), α-thioglycerol (m.w.:108.16) etc.

To culture bovine embryos (in vitro fertilized etc.) up to blastocyst stage low molecular thiol compounds mentioned above must be added to the medium. The effective concentration of the compounds in the medium is within the range of 10–100 μM preferably 10–50 μM .

For the medium, Tissue Culture Medium (TCM)-199, DMEM, MEM, CMRL 1066 and NCTC 109 etc. are used and those media are supplemented with 10% (V/V) fetal calf serum (FCS), calf serum (CS), bovine serum albumin (BSA), polyvinylpyrrolidone (PVP) and polyvinylalchohol (PVA) etc.

To transport bovine embryos without decreasing their viability the addition of low molecular thiol compounds at concentrations of 10–150 μM , preferably 100–150 μM to the medium of transportation is necessary.

For the medium of utilizing transportation, modified TCM-199 etc. supplemented with 20% calf serum are used.

According to the present invention, it is possible to culture bovine embryos up to blastocyst stage efficiently in the medium containing low molecular thiol compound without in vivo culture or coculture using feeder cells.

Also when low molecular thiol compound is added to the transportation medium for bovine embryos, almost 100% embryos are still viable after long distant transportation. This transportation method makes it possible to transfer embryos to recipient cows as soon as they are transported to the place where embryo transfer is carried out. With this method, there is no need for a facility for thawing of frozen embryos or judgment of viability of frozen-thawed embryos.

This invention is explained in detail by the following Examples.

EXAMPLE 1

Bovine ovaries were obtained at a slaughterhouse and transported to the laboratory. Oocytes from follicles (2–6 mm in diameter) were aspirated with a 5-ml syringe equipped with an 18-gauge needle and then cultured for 24 hours in TCM-199 supplemented with 10% fetal calf serum (FCS), luteinizing hormone (LH) and follicle stimulating hormone (FSH). After maturation culture, oocytes were transferred to the fertilization medium (Brackette and Oliphant solution: BO) containing heparin (10 μg/ml), caffeine (2.5 mM) and bovine serum albumin (10 mg/ml), and inseminated in vitro with frozen-thawed bull spermatozoa at a concentration of $1 \times 10^7$ cells/ml. After 5 hours of insemination, fertilized oocytes were transferred to TCM-199 containing 10% fetal calf serum and cultured for 40 hours up to 6–8 cell stage. These 6–8 cell embryos were freed from adhering cumulus cells and then used for culture experiments.

Embryos (6–8 cell stage) were transferred to 1) TCM-199 supplemented with 10% FCS (TCM-199+FCS) as control, 2) supplemented with 10 μM β-ME, 3) 50 μM β-ME, 4) 10 μM cysteamine and 5) 50 μM cysteamine, and cultured for 7 days without any feeder cells. After 7 days of culture, the developmental stage of embryos was observed and recorded. The results are shown in Table 1. As shown in Table 1, the percentage of embryos developed to the blastocyst stage was significantly higher when cultured in TCM-199+FCS containing 10 μM β-ME (24.3%), 50 μM β-ME (34.5%), 10 μM cysteamine (18.9%) and 50 μM cysteamine (29.4%) than when they were cultured in TCM-199+FCS alone (control).

TABLE 1

Effect of a thiol compound on development of in vitro cultured embryos to blastocyst stage

| Culture medium | No. of embryos cultured | No. of embryos developed to blastocyst stage |
|---|---|---|
| TCM-199 + FCS | 42 | 3 (7.1) |
| TCM-199 + FCS + 10 μM β-ME | 74 | 18 (24.3) * |
| TCM-199 + FCS + 50 μM β-ME | 84 | 29 (34.5) ** |
| TCM-199 + FCS + 10 μM cysteamine | 90 | 17 (18.9) |
| TCM-199 + FCS + 50 μM cysteamine | 119 | 35 (29.4) ** |

* $P < 0.05$, ** $P < 0.1$

EXAMPLE 2

Bovine embryos developed to blastocyst stage after 7 days of culture according to Example 1 were used for transportation experiments. Embryos were transferred to transportation medium, modified TCM-199 supplemented with 20% calf serum as control, and supplemented with 10, 50, 100 and 150 μM of β-ME. Embryos in each transportation medium were put in 0.25 ml straw, and then transported in a warm box at 37° C. from Tokyo to Sapporo. After transportation, viability of embryos was examined and the embryos applicable for embryo transfer were selected. The selected embryos were nonsurgically transferred to recipient cows and the pregnancy of them was diagnosed. The results are shown in Table 2.

As shown in Table 2, the percentage of excellent embryos after transportation was significantly higher when transported in modified TCM-199+CS containing β-ME (>80%) than when they were transported in modified TCM-199+CS alone (53.6%). Specially all the embryos transported in modified TCM-199 supplemented with 100 and 150 μM β-ME were excellent, showing high viability.

TABLE 2

Effect of a thiol compound on transportation of in vitro cultured embryos

| Concentration of β-ME | No. of embryos transported | No. of embryos survived | No. of excellent embryos |
|---|---|---|---|
| 0 | 40 | 28(70) | 15(53.6) |
| 10 | 40 | 40(100) | 32(80.0)* |
| 50 | 40 | 40(100) | 35(87.5)* |
| 100 | 43 | 43(100) | 43(100)* |
| 150 | 39 | 39(100) | 39(100)* |

*$P < 0.05$

Duration of transportation is 17–21 h. (mean 18.3 h)

Embryos transported in modified TCM-199+CS containing β-ME were transferred to recipient cows and the pregnancy of them was diagnosed. The results are showing Table 3.

As shown in Table 3, 21 of 36 recipient cows were pregnant. β-ME is proved not to be harmful to embryos.

TABLE 3

Effect of a thiol compound on fertility of in vitro cultured embryos

| Medium | No. of cows transferred embryos | No. of cows pregnant |
|---|---|---|
| TCM-199 + 20% CS | 35 | 19(54.3) |
| TCM-199 + 20% CS + 150M μM β-ME | 36 | 21(58.3) |

What is claimed is:

1. A method of transporting bovine embryos developed to the blastocyst stage in a culture medium and which have not been frozen which comprises transferring the embryos from the culture medium to a transportation medium and transporting said bovine embryos in the transportation medium, the transportation medium comprising a thiol compound selected from the group consisting of β-mercaptoethanol, β-mercaptoethylamine, glutathione, dithiothreitol and α-thioglycerol, while maintained in non-frozen condition, the transporting being from a culturing laboratory to a location for carrying out embryo transfer.

2. The method of claim 1, wherein said bovine embryos are transported while maintained at 37° C.

3. The method of claim 2, wherein the thiol compound is present at a concentration of 10–150 μM in the transportation medium.

4. The method of claim 3, wherein the thiol compound is β-mercaptoethanol.

5. The method of claim 1, wherein the thiol compound is β-mercaptoethanol.

* * * * *